(12) United States Patent
Reeder et al.

(10) Patent No.: US 11,571,309 B2
(45) Date of Patent: Feb. 7, 2023

(54) ORTHOPAEDIC SURGICAL INSTRUMENT SYSTEM AND A METHOD OF TRIALING AN ORTHOPAEDIC PROSTHETIC ASSEMBLY

(71) Applicant: DePuy Ireland Unlimited Company

(72) Inventors: Nathan C. Reeder, Warsaw, IN (US);
Aaron J. Matyas, Ft. Wayne, IN (US);
Lauren A. Ferris, Elkhart, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 0 days.

(21) Appl. No.: 17/038,710

(22) Filed: Sep. 30, 2020

(65) Prior Publication Data
US 2022/0096244 A1    Mar. 31, 2022

(51) Int. Cl.
*A61F 2/38*    (2006.01)
*A61F 2/30*    (2006.01)

(52) U.S. Cl.
CPC ............ *A61F 2/3845* (2013.01); *A61F 2/389* (2013.01); *A61F 2/3859* (2013.01); *A61F 2002/30878* (2013.01)

(58) Field of Classification Search
CPC ...... A61F 2/3845; A61F 2/3859; A61F 2/389; A61F 2002/30878
See application file for complete search history.

(56) References Cited

U.S. PATENT DOCUMENTS

| 10,722,372 B2 | 7/2020 | Collazo |
| 2005/0107886 A1* | 5/2005 | Crabtree ............... A61F 2/3859 623/20.29 |

* cited by examiner

*Primary Examiner* — Bruce E Snow
(74) *Attorney, Agent, or Firm* — Barnes & Thornburg LLP

(57) ABSTRACT

An orthopaedic surgical instrument system includes a hinged tibial insert trial and a tibial base trial. A post adapter is sized to be positioned over a post of the tibial base trial and to be positioned in a central opening defined in the hinged tibial insert trial. The hinged tibial insert trial includes a housing configured to be received in a femoral component and a button mechanism to selectively secure the hinged tibial insert trial to the femoral component. The system may include a shim trial sized to be attached to an inferior surface of the hinged tibial insert trial.

10 Claims, 14 Drawing Sheets

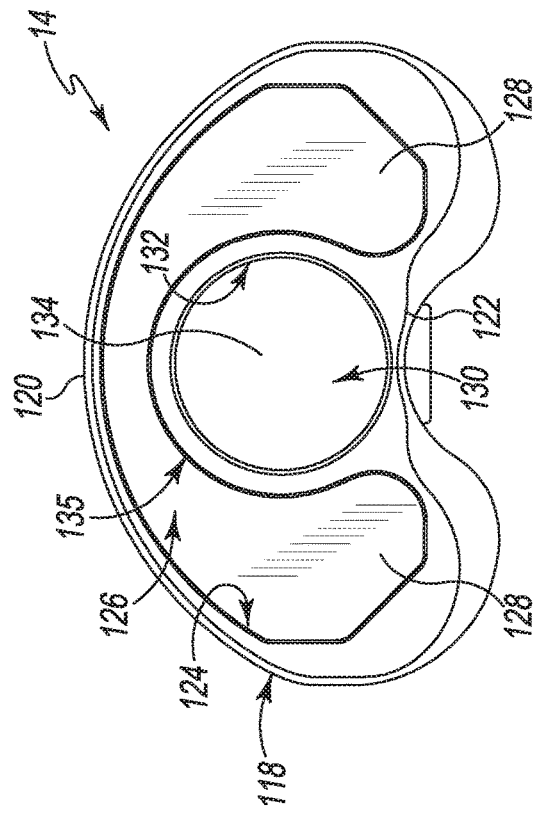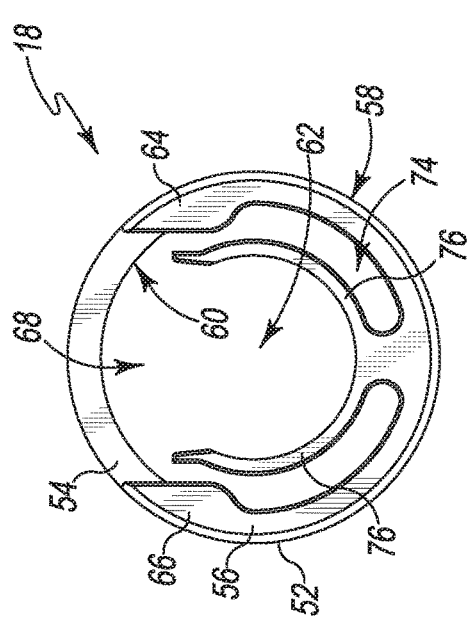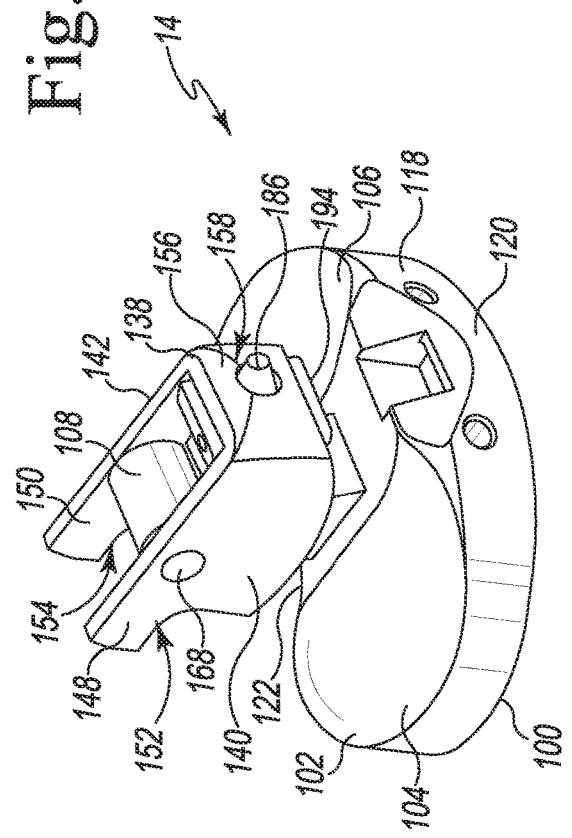

ORTHOPAEDIC SURGICAL INSTRUMENT SYSTEM AND A METHOD OF TRIALING AN ORTHOPAEDIC PROSTHETIC ASSEMBLY

TECHNICAL FIELD

The present disclosure relates generally to orthopaedic surgical instruments, and particularly to a tibial trial component for use in trialing an orthopaedic prosthetic.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. In a revision knee surgery, the previously-implanted knee prosthesis, sometimes referred to as a "primary knee prosthesis," is surgically removed and a replacement or revision knee prosthesis is implanted. A typical knee prosthesis includes a tibial tray, a femoral component, and a polymer insert or bearing positioned between the tibial tray and the femoral component. In some cases when soft tissue may not be adequate, a hinged knee prosthesis is implanted, where the polymer insert or bearing links the femoral component to the insert to allow for flexion and extension of the knee. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

During joint arthroplasty, trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, a tibial insert trial that may be used to size and select a prosthetic tibial insert, and a stem trial that may be used to size and select a prosthetic stem component.

SUMMARY

According to one aspect of the disclosure, an orthopaedic surgical instrument system includes a tibial base trial, a hinged tibial insert trial, a post adapter, and a femoral component. The tibial base trial includes a plate configured to be positioned on a proximal end of a patient's tibia and a post extending outwardly from a superior surface of the plate. The hinged tibial insert trial includes an inferior surface configured to confront the superior surface of the plate. The hinged tibial insert further includes a pair of curved surfaces positioned opposite the inferior surface, a spine positioned between the pair of curved surfaces, a housing hingedly coupled to the spine and including a button mechanism having an elongated plunger pin, and a central opening defined in the inferior surface. The post adapter is sized to be positioned in the central opening defined in the hinged tibial insert trial. The post adapter includes an outer wall and an aperture defined in the outer wall that is sized to receive the post of the tibial base trial. The femoral component includes a pair of curved surfaces configured to confront the pair of curved surfaces of the hinged tibial insert trial. The femoral component further includes anterior flange positioned between the pair of curved surfaces, a femoral box defined between the pair of curved surfaces and configured to receive the housing of the hinged tibial insert trial, and a pocket defined in an inner wall of the anterior flange and configured to receive a first end of the elongated plunger pin. The button mechanism is operable to retract the first end of the elongated plunger pin within the housing.

In an embodiment, the post adapter includes a locking tab positioned in a central passageway defined in the post adapter. In an embodiment, the post includes a stem extending outwardly from the plate to the superior flange, and the locking tab includes a pair of arms configured to engage the stem of the post, wherein each arm of the pair of arms is a spring clip.

In an embodiment, the housing includes a medial wall having a transverse bore defined in the medial wall and extending in a medial-lateral direction, and a lateral wall having a transverse bore defined in the lateral wall and extending in the medial-lateral direction. The spine includes a transverse bore extending in the medial-lateral direction. The hinged tibial insert trial includes an elongated pin positioned in the transverse bores of the housing and the spine to couple the housing to the spine. In an embodiment, the housing of the hinged tibial insert trial is configured to rotate about an axis extending through the elongated pin.

In an embodiment, the orthopaedic surgical instrument system further includes a trial shim including an inferior surface configured to confront the superior surface of the plate, a superior surface including a superior plateau sized to be received by a recess defined in the inferior surface of the hinged tibial insert trial, and a central passageway defined in the trial shim and sized to receive the post adapter.

In an embodiment, the housing includes a hook extending posteriorly and including a curved inferior surface. The femoral component includes a shelf extending into the femoral box and including a curved superior surface configured to confront the curved inferior surface of the housing. In an embodiment, the femoral component comprises a prosthetic implant.

In an embodiment, the housing includes an anterior wall having a bore defined in the anterior wall. The first end of the plunger pin selectively extends through the bore in the anterior wall, and the button mechanism includes a spring configured to bias the first end of the plunger pin to extend through the bore. In an embodiment, the housing includes a medial wall and a lateral wall, wherein the medial wall, the lateral wall, and the anterior wall cooperate to define a button chamber accessible through the bore in the anterior wall, and wherein the button mechanism is positioned within the button chamber. The button mechanism includes a button plate coupled to the plunger pin and extending through an inferior opening in the button chamber.

According to another aspect, an orthopaedic surgical instrument comprises a hinged tibial insert trial that includes an inferior surface configured to confront a superior surface of a tibial base trial, a pair of curved surfaces positioned opposite the inferior surface, a central opening defined in the inferior surface, a spine positioned between the pair of curved surfaces, and a housing hingedly coupled to the spine and including a button mechanism having an elongated plunger pin having a first end that selectively extends out of the housing, wherein the button mechanism is operable to retract the first end of the elongated plunger pin within the housing.

In an embodiment, the orthopaedic surgical instrument further includes an elongated pin, wherein the housing includes a medial wall having a transverse bore defined in the medial wall and extending in a medial-lateral direction and a lateral wall having a transverse bore defined in the lateral wall and extending in the medial-lateral direction. The spine includes a transverse bore extending in the medial-lateral direction, and the elongated pin is positioned in the transverse bores of the housing and the spine to couple the housing to the spine. In an embodiment, the housing is configured to rotate about an axis extending through the elongated pin.

In an embodiment, the housing includes an anterior wall having a bore defined in the anterior wall, the first end of the plunger pin selectively extends through the bore in the anterior wall, and the button mechanism includes a spring configured to bias the first end of the plunger pin to extend through the bore. In an embodiment, the housing includes a medial wall and a lateral wall, wherein the medial wall, the lateral wall, and the anterior wall cooperate to define a button chamber accessible through the bore in the anterior wall, and wherein the button mechanism is positioned within the button chamber. The button mechanism includes a button plate coupled to the plunger pin and extending through an inferior opening in the button chamber. In an embodiment, the spine includes a bore extending generally in an anterior-posterior direction and configured to receive a shank of the plunger pin.

According to another aspect, a method of assembling a surgical instrument system includes clipping a base post adapter onto a post of a tibial base trial, wherein the tibial base trial is positioned on a proximal end of a patient's tibia; placing a hinged tibial insert trial on the base post adapter in response to clipping the base post adapter; positioning the patient's knee joint in less than about 45 degrees of flexion in response to placing the hinged tibial insert trial; depressing a button mechanism of the hinged tibial insert trial causing retraction of a plunger pin; inserting a housing of the hinged tibial insert trial into a femoral box defined in a femoral component through a gap defined between a pair of curved surfaces of the femoral component while depressing the button mechanism and in response to positioning the patient's knee joint; and releasing the button mechanism in response to inserting the housing.

In an embodiment, the method further includes moving the patient's knee joint through a range of motion including extension and flexion in response to releasing the button mechanism. In an embodiment, the method further includes positioning the patient's knee joint in less than about 45 degrees of flexion in response to moving the patient's knee joint through the range of motion; and removing the housing of the hinged tibial insert trial from the femoral box while depressing the button mechanism and in response to positioning the patient's knee joint.

In an embodiment, the method further includes attaching a trial shim to an inferior surface of the hinged tibial insert trial; wherein placing the hinged tibial insert trial on the base post adapter includes placing the hinged tibial insert trial and the trial shim on the base post adapter in response to attaching the trial shim.

BRIEF DESCRIPTION

The detailed description particularly refers to the following figures, in which:

FIG. 2 is a bottom plan view of a base post adapter shown in FIG. 1;

FIG. 3 is a bottom plan view of a hinged tibial insert trial shown in FIG. 1;

FIG. 4 is a perspective view of the hinged tibial insert trial shown in FIG. 1;

DETAILED DESCRIPTION

Figure 1:
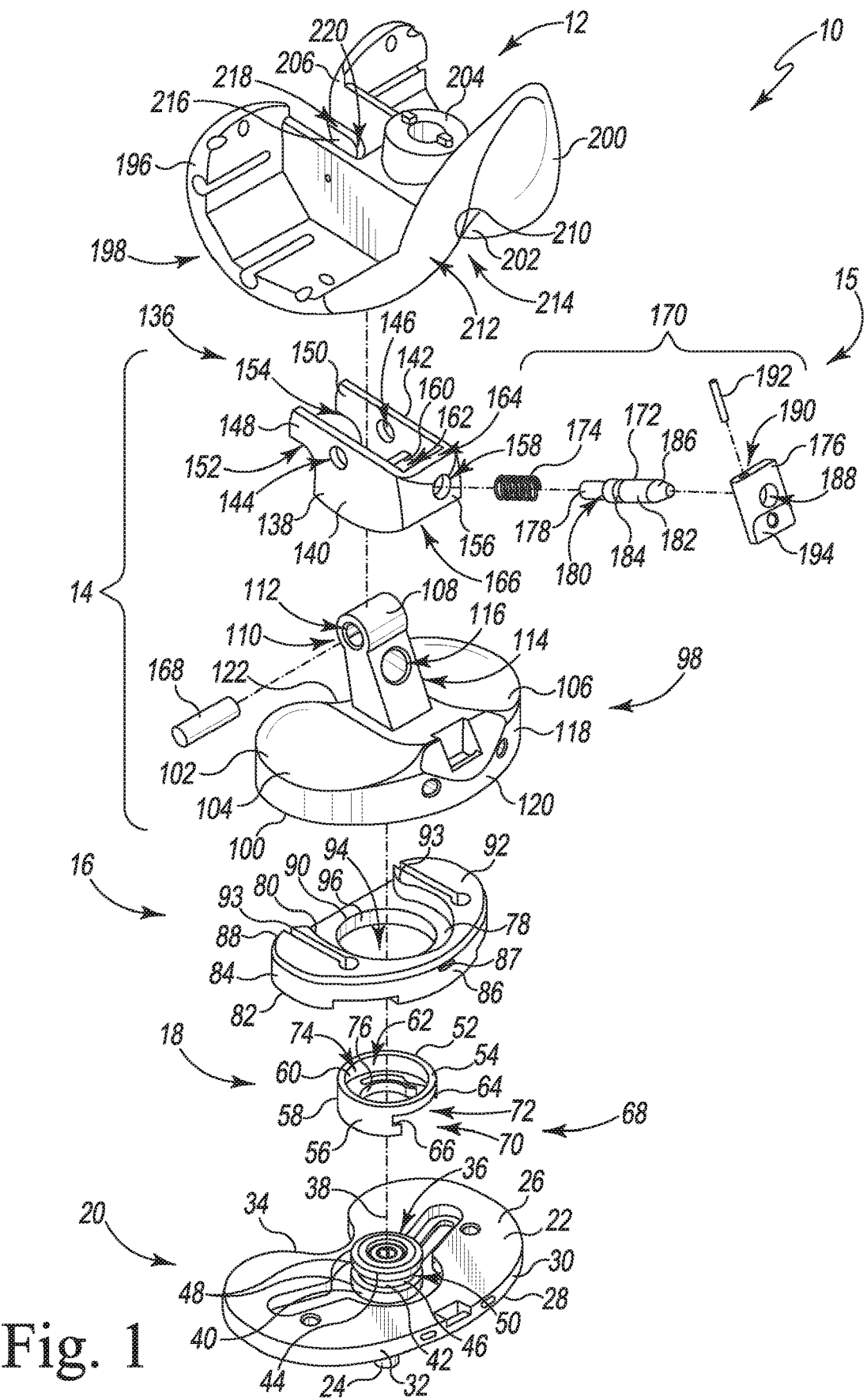
FIG. 1 is an exploded view of an orthopaedic surgical instrument system in accordance with one embodiment.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIGS. 1-6 an orthopaedic surgical instrument system 10 includes a tibial base trial component 20, a tibial base post adapter 18, and a hinged tibial insert trial component 14 configured to be selectively coupled to the tibial base trial 20 using the tibial base post adapter 18. The tibial base trial component 20 and the hinged tibial insert trial component 14 may be utilized with a femoral component 12 to size and select a tibial prosthesis for implantation into a patient's surgically-prepared tibia. The femoral component 12 may be a femoral trial component as shown in FIG. 1 or, in some embodiments, a femoral implant or other femoral component. It should be appreciated that the system 10 may include a number of trial components 14, 20 and femoral trial components of different sizes to accommodate a range of patient anatomies.

As described in greater detail below, the base post adapter 18 is configured to removably secure to the tibial base trial 20, and the hinged tibial insert trial 14 and/or a trial shim 16 attached to the hinged tibial insert trial 14 may be positioned on the base post adapter 18. It should be understood that in some embodiments, the hinged tibial insert trial 14 and the trial shim 16 may be combined in a single tibial insert trial component. The system 10 may include multiple such combined tibial insert trial components, for example each having different sizes and/or thicknesses. In some embodiments, the base post adapter 18 may also be included in such a combined tibial insert trial component.

The hinged tibial insert trial 14 is configured to be removably secured to the femoral component 12 by a retention device 15, which is illustratively embodied as a pushbutton release system 170. During a surgical procedure, the surgeon may evaluate the range of motion of the patient's leg with the base trial component 20, the hinged tibial insert trial component 14, and the femoral component 12 positioned in the knee joint, assessing, among other things, the stability of the knee and the displacement of the joint. The hinged tibial insert trial 14 is configured to be detached from the femoral component 12 and from the base post adapter 18 during the surgical procedure and replaced with a hinged tibial insert trial 14 and/or shim 16 of different size to permit the surgeon to evaluate a range of possible implant sizes and select the one that provides the best performance.

The tibial base trial component 20 is configured to be positioned on a surgically-prepared proximal end of a patient's tibia. In the illustrative embodiment, the base trial 20 includes a plate 22 shaped to be positioned on a proximal end of a patient's tibia. The plate 22 has a superior surface 26, an inferior surface 28, and an outer side wall 30 extending between the surfaces 26, 28. The outer side wall 30 has an anterior section 32 and a posterior section 34 shaped to match a proximal end of a resected tibia. In the illustrative embodiment, the anterior section 32 of the side wall 30 is convexly curved, and the posterior section 34 is concavely curved. It should be appreciated that the tibial base trial 20 may be formed in a number of different sizes to accommodate tibias of various sizes.

The tibial base trial 20 may receive a pin 24, which when attached to the tibial base trial 20 extends downwardly from the inferior surface 28 of the plate 22. The pin 24 is sized to be received in a notch of a surgical instrument inserted into the proximal end of the patient's tibia. Such instruments may include, for example, an elongated broach or stem trial component sized to be positioned in a patient's intramedullary canal. The plate 22 also includes a number of fastener guides. Each fastener guide illustrative includes a bore configured to receive a fastener such as a fixation pin, which may be utilized to secure the tibial base trial 20 to the proximal end of the patient's tibia.

The tibial base trial 20 includes a post 36 that extends outwardly from the superior surface 26 of the plate 22 along a longitudinal axis 38. The post 36 is configured to secure to the base post adapter 18. The post 36 includes an inferior flange 40 extending from the superior surface 26 of the plate 22, a stem 42 extending from the inferior flange 40, and a superior flange 44 extending from the stem 42 to a proximal end of the post 36. The stem 42 includes an outer surface 46 having a radius from the longitudinal axis 38 of the post 36.

The flanges 40, 44 each include an outer surface 48 having a radius from the longitudinal axis 38. The radius of the outer surfaces 48 is larger than the radius of the outer surface 46. Thus, a channel 50 is defined between the inferior flange 40 and the superior flange 44. In particular, the channel 50 is defined between an inferior surface of the superior flange 44 and a superior surface of the inferior flange 40. As described below, a locking mechanism of the base post adapter 18 is configured to engage the stem 42 of the post 36 within the channel 50.

As shown in FIGS. 1-2, the base post adapter 18 of the hinged tibial insert trial component 14 includes an annular body 52 having a superior ring 54 and an inferior extension 56 extending inferiorly from the superior ring 54. The annular body 52 includes an outer surface 58 and a curved inner surface 60 positioned opposite the outer surface 58. The inner surface 60 defines a central passageway 62 through the base post adapter 18 that is sized to be positioned over the post 36 of the tibial base trial 20.

The inferior extension 56 includes a pair of curved arms 64, 66 that extend around the central passageway 62, and an aperture 68 is defined between the arms 64, 66. The aperture 68 includes a slot 70 positioned at an inferior end of the aperture 68, and another slot 72 positioned superior to the slot 70. The slot 70 is sized to receive the stem 42 of the post 36, and the slot 72 is sized to receive the superior flange 44 of the post 36.

In some embodiment, a locking tab 74 may be positioned within the central passageway 62. The locking tab 74 includes a trunk extending inward from the inner surface 60 into the central passageway 62. The locking tab 74 also includes a pair of arms 76 extending from the trunk 66. Each arm 76 includes a curved inner surface that corresponds to the outer surface 46 of the stem 42, and a gap is formed between an outer surface of each arm 76 and the curved inner surface 60. An opening is defined between the arms 76 such that each arm 76 is configured as a spring clip that can deflect into the respective gap to position the locking tab 74 on the post 36 of the tibial base trial 20. When the base post adapter 18 is secured to the tibial base trial 20, the arms 76 of the locking tab 74 are configured to position within the channel 50 defined between the superior flange 44 and the inferior flange 40, as described below. Additionally or alternatively, in some embodiments the arms 64, 66 of the inferior extension 56 may be configured as spring clips configured to position within the channel 50.

As shown in FIG. 1, the instrument system 10 may include a trial shim 16 configured to be selectively attached to the hinged tibial insert trial 14. The shim 16 includes a plate 78 shaped to confront the superior surface 26 of the tibial base trial 20. The shim 16 has a superior surface 80, an inferior surface 82, and an outer side wall 84 extending between the surfaces 80, 82. It should be understood that in some embodiments, the system 10 may be assembled with one of a number of different trial shims 16. Each trial shim 16 may have a different thickness; that is, the outer side wall 84 of each trial shim 16 may have a different height.

The outer side wall 84 of the trial shim 16 further includes an anterior section 86 and a posterior section 88. In the illustrative embodiment, the anterior section 86 of the side wall 84 is convexly curved, and the posterior section 88 is concavely curved. An oval notch 87 is defined in the anterior section 86, and the posterior section 88 further includes a straight ledge 90. As described further below, the ledge 90 may provide a grip surface for a surgeon to use when assembling or disassembling the system 10.

The trial shim 16 further includes a superior plateau 92 positioned on the anterior section 86 of the outer side wall 84. A pair of locking tabs 93 extend posteriorly from the superior plateau 92 toward the posterior section 88. As described further below, the superior plateau 92 and the outer side wall 84 are sized to be received and retained by the hinged tibial insert trial 14. The oval notch 87 and the locking tabs 93 are configured to engage the hinged tibial insert trial 14. A central passageway 94 through the trial shim 16 is defined by an inner side wall 96. The central passageway 96 is sized to receive the outer surface 58 of the base post adapter 18.

The hinged tibial insert trial 14 includes a body 98 and a housing 136 that may be hingedly connected by an elongated pin 168. The body 98 has an inferior surface 100 and a superior surface 102. The inferior surface 100 of the hinged tibial insert trial 14 is configured to confront the superior surface 26 of the plate 22 or the superior surface 80 of the trial shim 16. The superior surface 102 includes a pair of curved surfaces 104, 106 positioned opposite the inferior surface 100 and configured to correspond to surfaces of the femoral component 12, as described below. A spine 108 is positioned between the curved surfaces 104, 106 and extends superiorly from the superior surface 102. A pin hole 110 extends medially-laterally between openings 112 formed in the spine 108. The pin hole 110 is configured to receive the elongated pin 168 (described further below) to secure the body 98 to the housing 136. The pin hole 110 may also be configured to receive bushings that are positioned in each opening 112. A plunger hole 114 extends anteriorly-posteriorly between openings 116 formed in the spine 108. The plunger hole 114 is configured to receive part of a button mechanism included in the housing 136 and described further below.

The body 98 includes an outer side wall 118 having an anterior section 120 that is shaped to match the anterior section 32 of the tibial base trial 20 and a posterior section 122 that is shaped to match the posterior section 34 of the base trial 20. As shown in FIG. 3, the body 98 further includes an inner side wall 124 positioned opposite the outer side wall 118 along a perimeter of the inferior surface 100. A recess 126 in the inferior surface 100 is defined by the inner side wall 124 and extends from the inferior surface 100 to a superior end wall 128. A central opening 130 in the inferior surface 100 is further defined by an inner side wall 132 and extends from the inferior surface 100 to a superior end wall 134. Similar to the central passageway 94 of the trial shim 16, the central opening 130 is sized to receive the outer surface 58 of the base post adapter 18. An intermediate side wall 135 is positioned opposite the inner side wall 132 and further defines a boundary of the recess 126. The recess 126 is configured to receive the superior plateau 92 of the shim 16, for example by a friction fit between the outer side wall 84 of the trial shim 16 and the inner side wall 124 of the body 98. The recess 126 is further configured to engage the locking tabs 93 of the trial shim 16. For example, in some embodiments, the locking tabs 93 may be embodied as spring clips that grip the intermediate side wall 135 and further retain the trial shim 16 against the body 98.

Referring again to FIG. 1, the housing 136 includes a body 138 having medial-lateral sides 140, 142. A pin hole 144, 146 extends through each of the respective sides 140, 142, and is configured to receive the elongated pin 168. As discussed further below, the housing 136 may be fixed to the body 98 by the pin 168, which allows the housing 136 to rotate relative to the body 98 about the pin 168. Each of the sides 140, 142 further includes a respective hook 148, 150 extending posteriorly from the respective side 140, 142. Each hook 148, 150 includes a respective curved inferior surface 152, 154.

As described above, the hinged tibial insert trial 14 is configured to be removably secured to the femoral trial component 12 by the retention device 15, which will now be described in greater detail. In the illustrative embodiment, the retention device 15 includes a retained fastener (e.g., a plunger pin 172) that is selectively engaged with a bore (e.g., pocket 222) to secure the femoral trial component 12 to the tibial insert trial 14. As shown in FIG. 1, the retention device is shown as a pushbutton release system 170 that includes the plunger pin 172. The body 138 of the housing 136 further includes an anterior wall 156 positioned between the sides 140, 142, and a bore 158, which is sized to receive the plunger pin 172, is defined through the anterior wall 156. Similarly, an inner wall 160 is positioned between the sides 140, 142 posterior to the anterior wall 156. A bore 162, also sized to receive the plunger pin 172, is defined through the inner wall 160. The sides 140, 142 and the walls 156, 160 cooperate to define a button chamber 164 within the housing 136. The button chamber 164 has an inferior opening 166 leading out of the housing 136.

Figure 6:
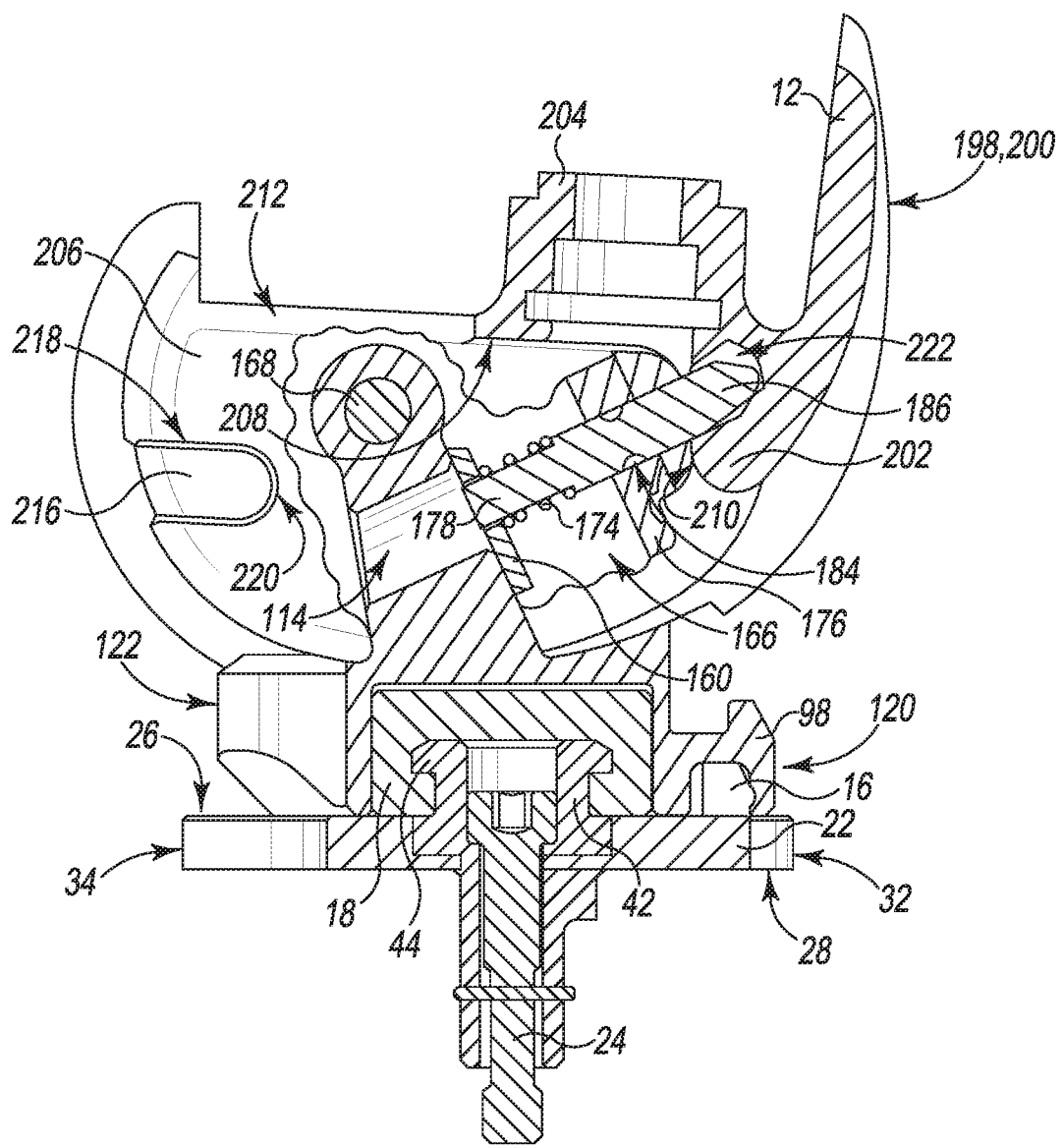
FIG. 6 is a cross-sectional view taken along the line 6-6 in FIG. 5.
Figure 7:
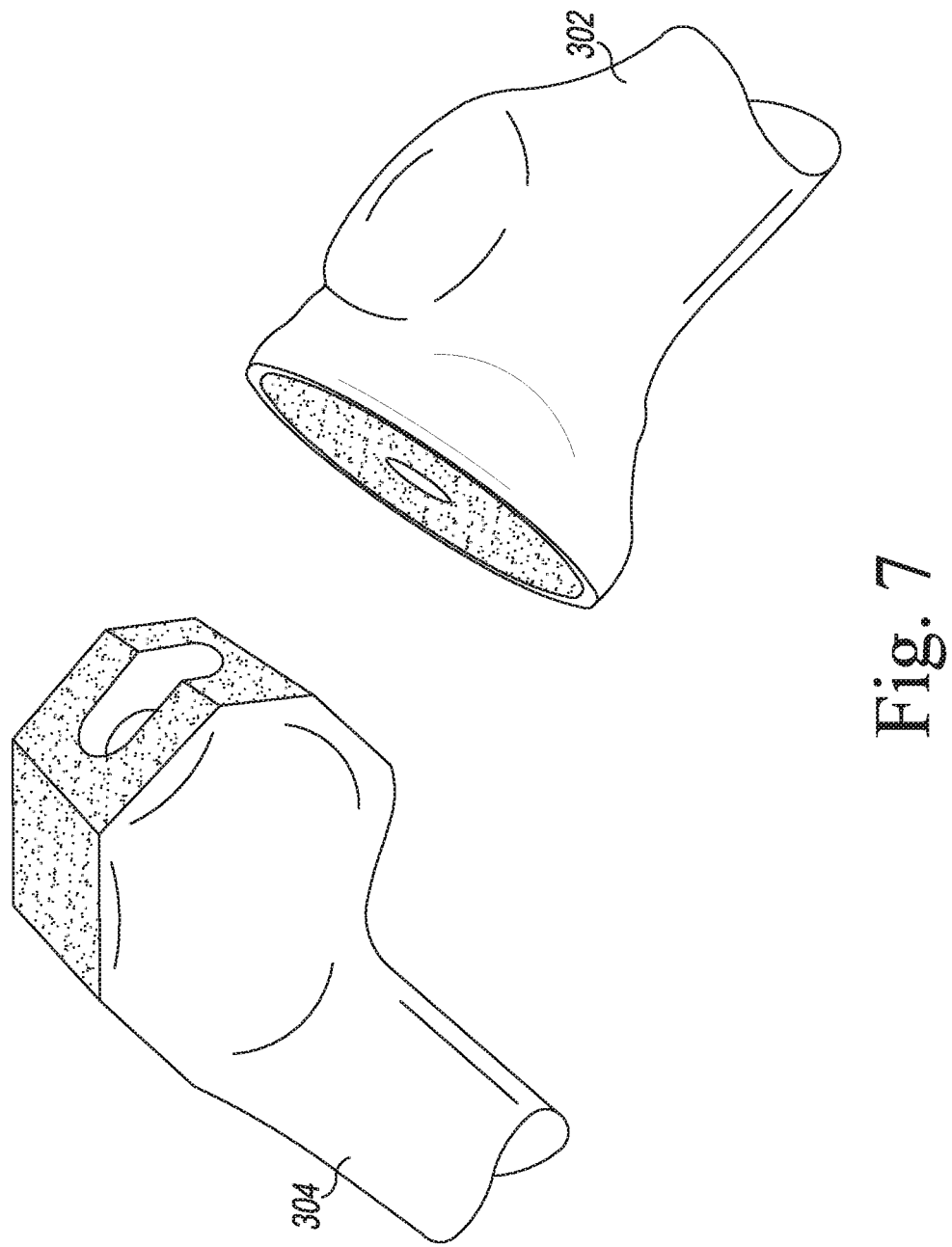
FIG. 7 is a perspective view of a patient's surgically prepared knee joint.

As shown in FIG. 6, when assembled, components of the pushbutton release system 170 may be positioned within the button chamber 164. As shown in FIGS. 1 and 6, the pushbutton release system 170 includes a button mechanism including the elongated plunger pin 172, a biasing element such as, for example, a spring 174, and an actuator such as, for example, a button 176. The plunger pin 172 extends from a posterior shank 178 to a cylindrical body 182 and then to a pointed end 186. A flat collar 180 separates the posterior shank 178 and the cylindrical body 182, and a circumferential groove 184 is defined in the cylindrical body 184.

The button 176 is generally flat, and a bore 188 is defined therethrough. A retaining pin channel 190 is defined through an opening in a superior end of the button 176. The retaining pin channel 190 opens into the bore 188 and is sized to receive a retaining pin or set screw 192. A button surface 194 is positioned on an inferior end of the button 176. As described below, a surgeon or other user may press the button surface 194 with a finger, forceps, or other tool to operate the pushbutton release system 170.

Referring again to FIG. 6, when assembled, the button 176 is positioned within the button chamber 164 with the button surface 194 extending out of the inferior opening 166. The plunger pin 172 is also positioned within the button chamber, and extends through the bores 162, 188, 158 of the inner wall 160, the button 176, and the anterior wall 156, respectively. The circumferential groove 184 of the plunger pin 172 is positioned within the bore 188, and the retaining pin 192 also extends through the retaining pin channel 190 into the bore 188. The retaining pin 192 thus retains the plunger pin 172 relative to the button 176. Although illustrated as a retaining pin 192, in other embodiments any technique may be used to retain the button 176 to the plunger pin 172. The spring 174 surrounds the posterior shank 178 and is positioned between the inner wall 160 and the collar 180, thus biasing the plunger pin 172 in an anterior direction toward the anterior wall 156 and biasing the button 176 into engagement with the inner surface of the anterior wall 156.

As shown, the button 176 is biased into a position at which the pointed end 186 of the plunger pin 172 extends outward (anteriorly) of the anterior wall 156 through the bore 158. In this position, the plunger pin 172 may engage the femoral component 12, as described further below. In use, a surgeon may depress the button surface 194 of the button 176, causing the plunger pin 172 to move posteriorly into the housing 136 into a different position and thereby retracting the pointed end 186 through the bore 158 into the button chamber 164. In this posterior position, engagement of the plunger pin 172 with the femoral component 12 is prevented. Further, although illustrated as a pointed end 186, it should be understood that the end 186 may be flat, round, or any other shape capable of engaging the femoral component 12, as described further below.

As shown in FIG. 4, when the hinged tibial insert trial 14 is assembled, the housing 136 is attached to the body 98 using the pin 168. The pin 168 passes through the pin holes 144, 146 of the housing 136 and through the pin hole 110 of the spine 108, allowing the housing 136 to rotate about an imaginary axis extending through the pin holes 110, 144, 146 along the pin 168. It should be understood that that the hinged tibial insert trial 14 may be assembled by a surgeon or other user and/or may be assembled pre-operatively (e.g., during manufacture).

Returning to FIG. 1, the femoral component 12 includes a body 196 having a pair of curved surfaces 198, 200 that are configured to articulate on the curved surfaces 104, 106 of the hinged tibial insert trial 14. An anterior flange 202 connects the curved surfaces 198, 200. A boss 204 extends superiorly from the body 196 and is configured to be attached to a surgical instrument such as a femoral broach, femoral stem trial, or other surgical instrument.

Figure 5:
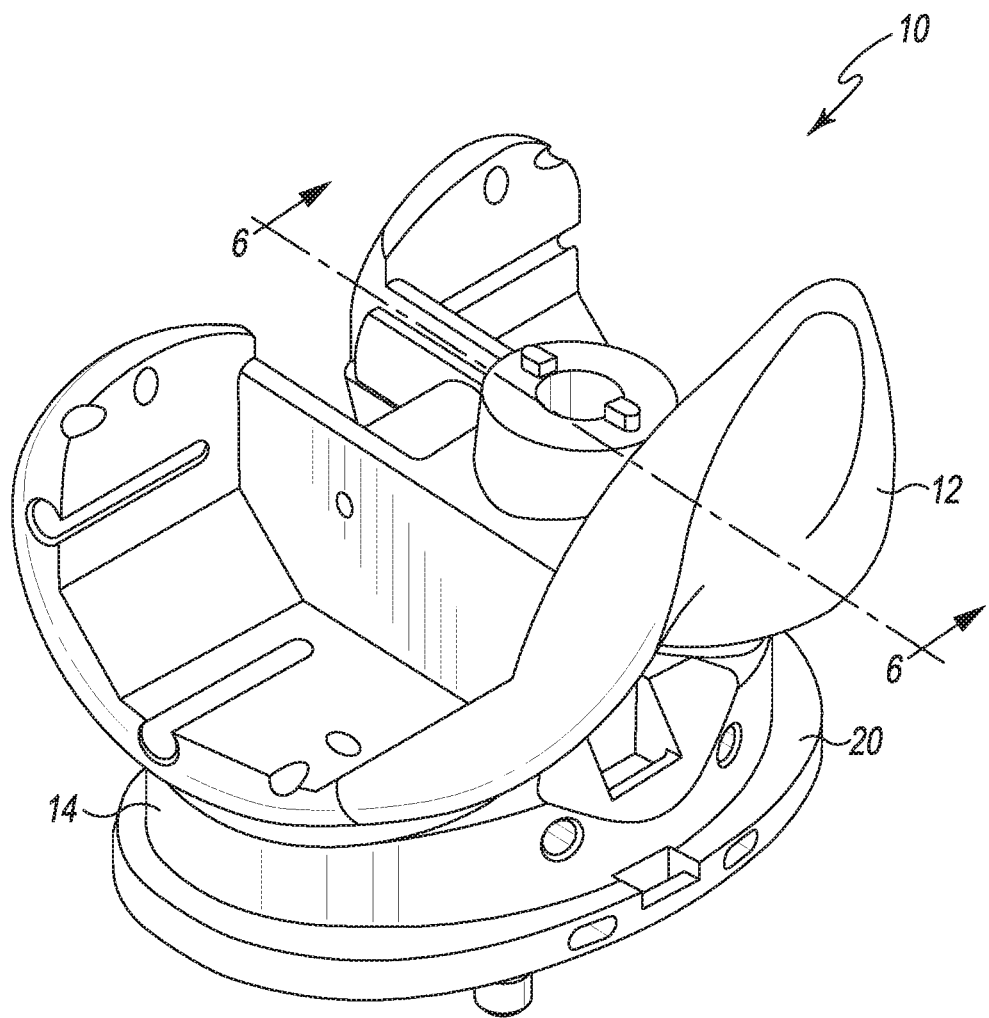
FIG. 5 is a perspective view of the orthopaedic surgical instrument system of FIG. 1.

Inner walls 206 extend inwardly from the curved surfaces 198, 200 toward a superior wall 208. Similarly, an inner wall 210 extends inwardly from the anterior flange 202 to the superior wall 208. The inner walls 206, 210 and the superior wall 208 define a femoral box 212. The femoral box 212 is accessible through an intercondylar notch 214, which is an aperture between the curved surfaces 198, 200. As shown in FIGS. 5-6 and described further below, the femoral box 212 is configured to receive the housing 136 of the hinged tibial insert trial 14. Each inner wall 206 includes a shelf 216 that projects into the femoral box 212 and is configured to receive a corresponding hook 148, 150 of the housing 136. As shown, each shelf 216 includes a flat superior surface 218 and a curved anterior surface 220. The surfaces 218, 220 are configured to engage the corresponding inferior surfaces 152, 154 of the hooks 148, 150. Although illustrated as including a pair of surfaces 218, 220 that engage a corresponding pair of hooks 148, 150 of the housing 136, it should be understood that in some embodiments, the femoral component 12 may include a single shelf surface projecting within the femoral box 212 that engages a corresponding hook of the housing 136.

As shown in FIG. 6, a pocket 222 is defined in the inner wall 210 of the anterior flange 202. The pocket 222 is configured to receive the pointed end 186 of the plunger pin 172 of the pushbutton release system 170. Thus, and as described further below, the housing 136 of the tibial insert trial component 14 may be removably secured within the femoral box 212 of the femoral trial component 12.

In an embodiment, multiple tibial insert trials 14 and trial shims 16 may be provided in different sizes and/or configurations. Because each tibial insert trial 14 and trial shim 16 are configured to be secured to the base post adapter 18, the surgeon is able to assemble a hinged tibial insert trial 14 and trial shim 16 assembly of one size and configuration, evaluate the performance of that assembly, and then modify the hinged tibial insert trial component 14 and/or the trial shim 16 as necessary to determine intraoperatively the type and configuration of the tibial insert component to be implanted.

Figure 8:
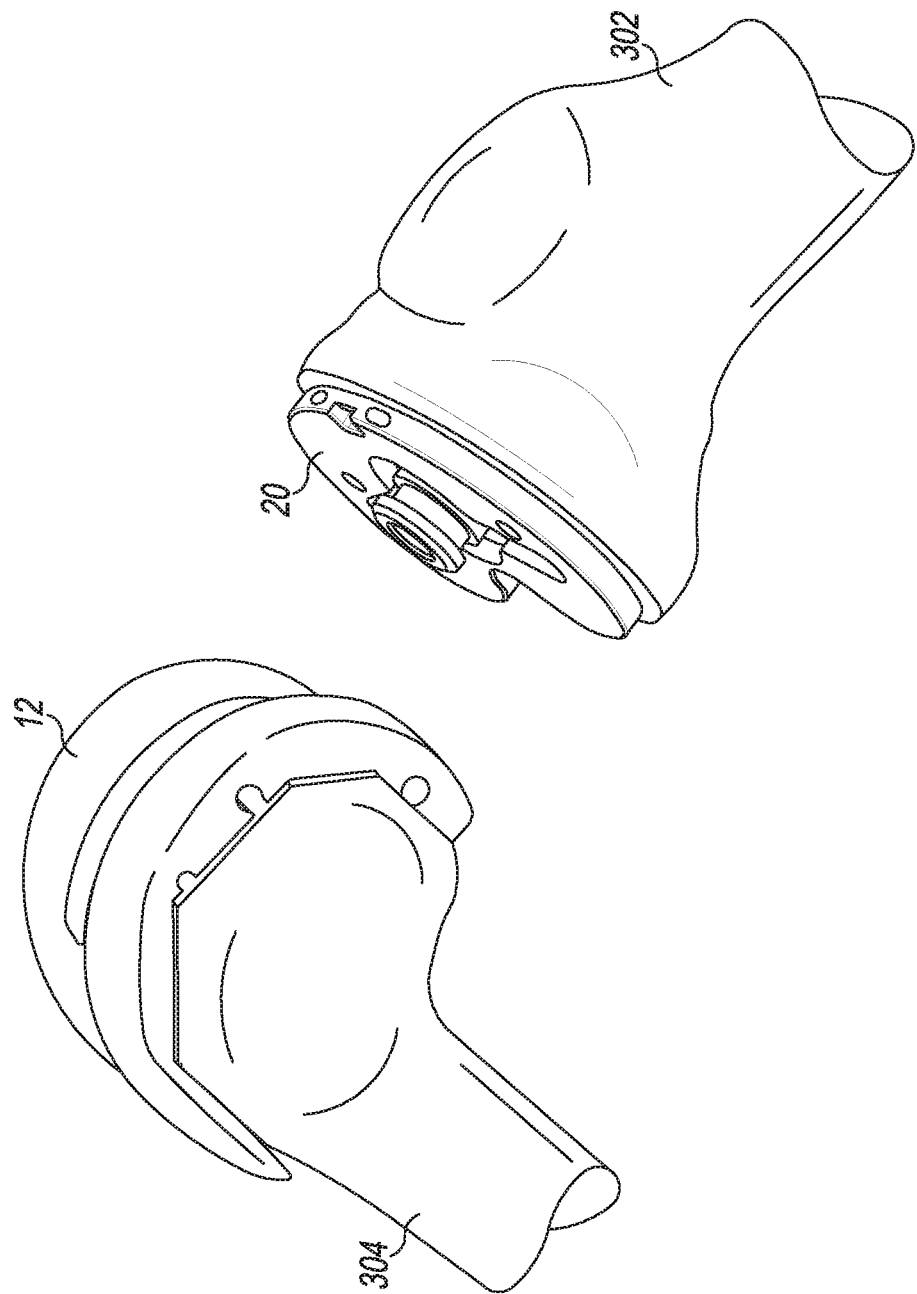
FIG. 8 is a perspective view of a femoral component and a tibial base trial of FIG. 1 positioned in the patient's surgically prepared knee joint.

Referring now to FIGS. 7-16, portions of an orthopaedic surgical procedure utilizing the system 10 are shown. The surgeon first performs a resection of the proximal end of the patient's tibia 302 to surgically prepare the tibia 302 for trial reduction. For example, the surgically-prepared proximal end of the patient's tibia 302 includes a resected surface configured to receive the tibial base trial 20. In an embodiment where the femoral component 12 is a trial component, the surgeon may also perform a resection of the distal end of the patient's femur 304 to surgically prepare the femur 304 for trial reduction. In an embodiment where the femoral component 12 is a primary femoral component (not shown) or other femoral implant, the surgeon may trial the hinged tibial insert trial component 14 with the primary femoral component or other femoral implant. As shown in FIG. 8, in the illustrative embodiment, the surgeon positions the tibial base trial 20 on the resected surface of the patient's tibia 302 and positions the femoral trial component 12 on the resected surface of the patient's femur 304.

Figure 9:
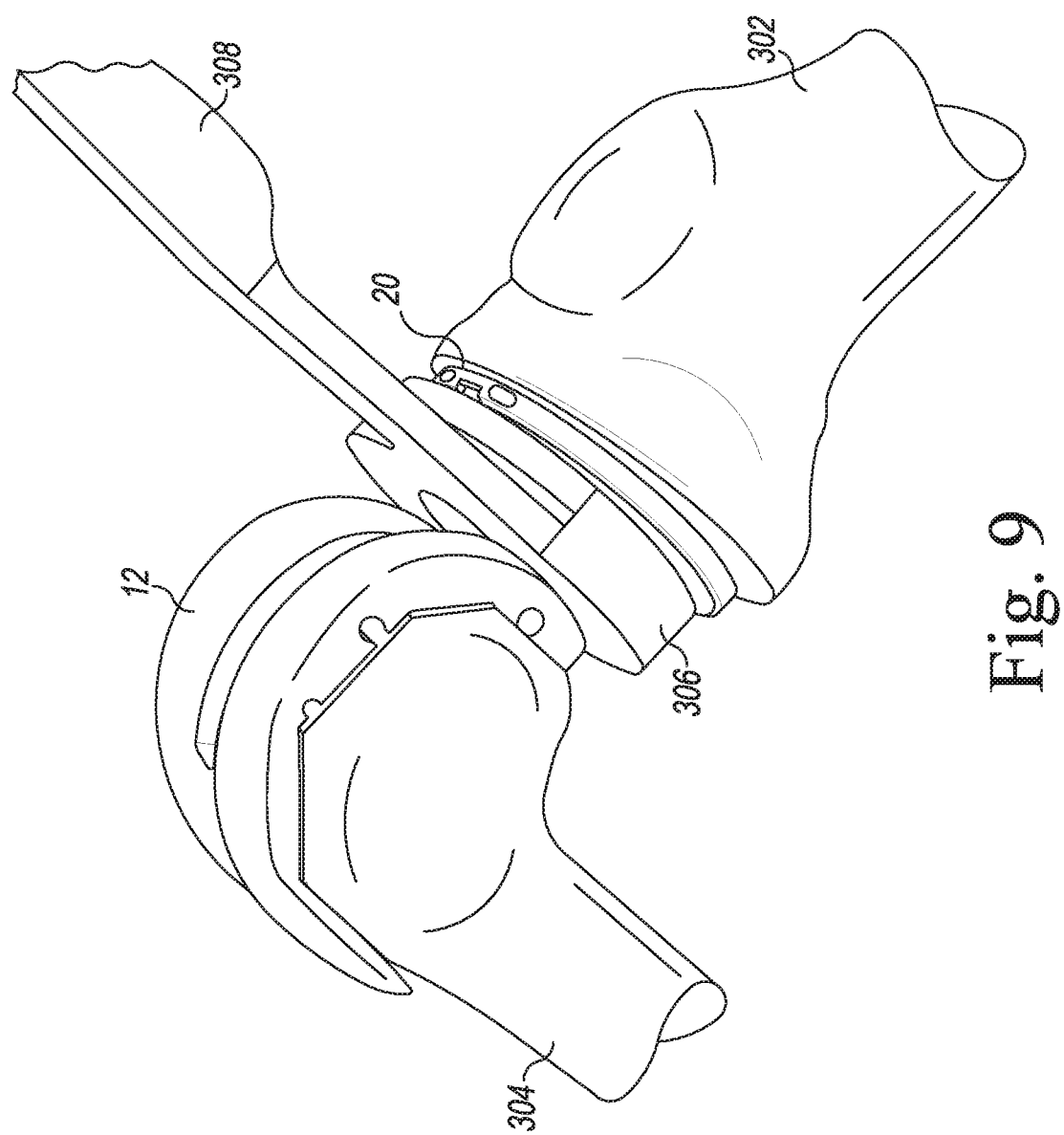
FIG. 9 is a perspective view of a spacer block inserted in the patient's knee joint.

After placing the tibial base trial 20 on the patient's tibia 302 and the femoral component 12 on the patient's femur 304, the surgeon evaluates the joint space. As illustrated in FIG. 9, the surgeon may insert a spacer block 306 of a joint distractor 308 into the patient's knee joint to evaluate the joint gap. The surgeon may evaluate the gap in flexion or extension. Typically, the patient's knee joint is distracted in extension an amount necessary to establish a generally rectangular joint gap.

Figure 10:
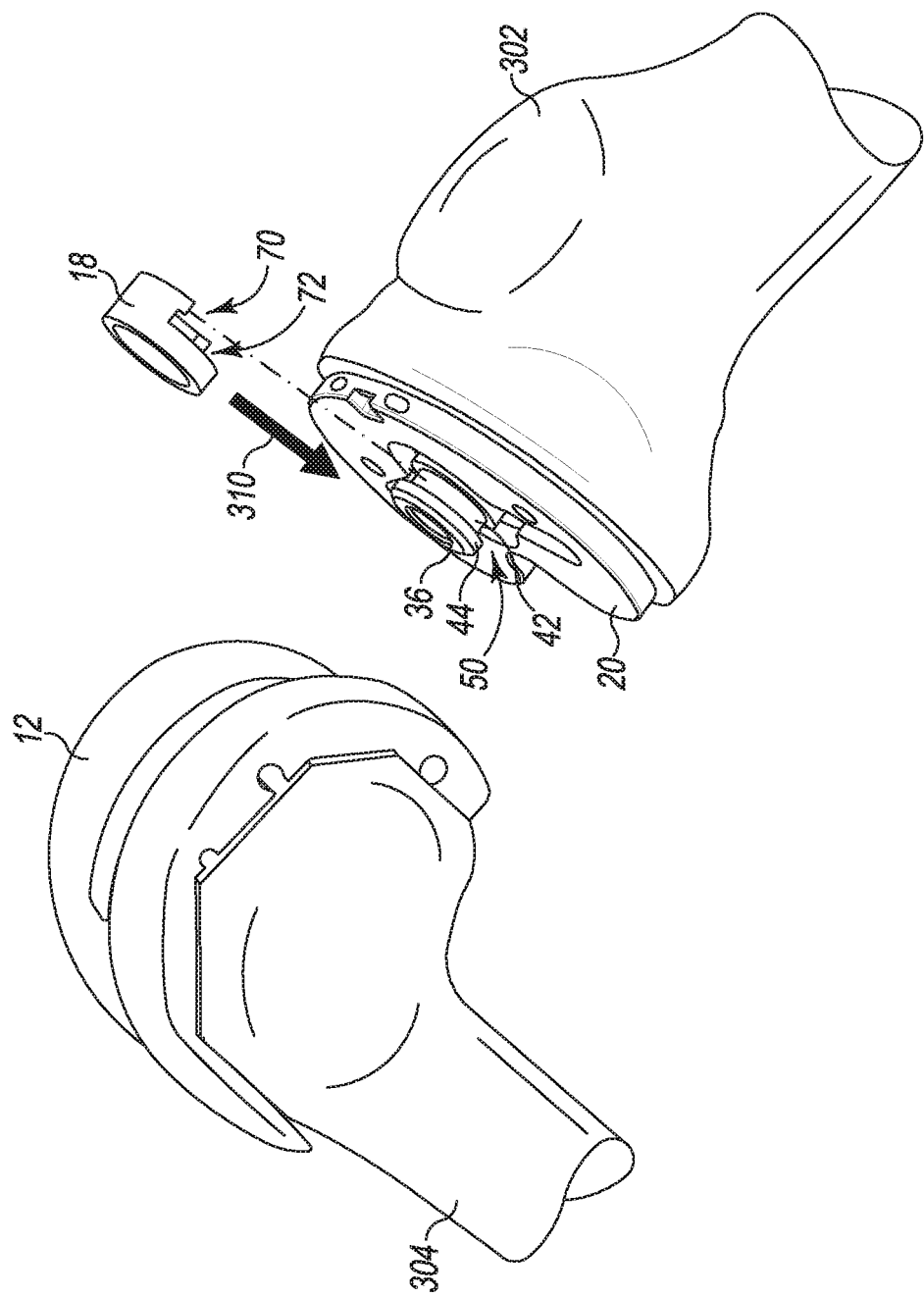
FIG. 10 is a perspective view of a base trial post adapter being attached to the tibial base trial of FIGS. 8-9.

After evaluating the joint space, the surgeon may perform an initial trial reduction with the instrument system 10. In doing so, the surgeon uses the system 10 to evaluate and check the stability and kinematics of the patient's femur 304 and tibia 302 for implantation of a hinged knee prosthesis. As illustrated in FIG. 10, the surgeon advances the base post adapter 18 in the direction indicated by arrow 310 in order to clip the base post adapter 18 onto the post 36 of the tibial base trial 20. As shown, the post 36 is received in the aperture 68, and in particular the superior flange 44 of the post 36 is received in the superior slot 72, and the stem 42 of the post 36 is received in the inferior slot 70.

As the base post adapter 18 is advanced, the post 36 passes through the opening between the arms 76 of the locking tab 74. The arms 76 of the locking tab 74 are received within the channel 50 defined between the superior flange 44 of the post 36 and the inferior flange 40 of the tibial base trial 20. The arms 76 of the locking tab 74 deflect outward so that the stem 42 of the post 36 is received in the opening defined between the arms 76. The arms 76 spring back to their original position to engage the stem 42 of the post 36 to secure the locking tab 74 to the post 36, thereby preventing movement of the base post adapter 18 in an inferior-superior direction relative to the tibial base trial 20.

Figure 11:
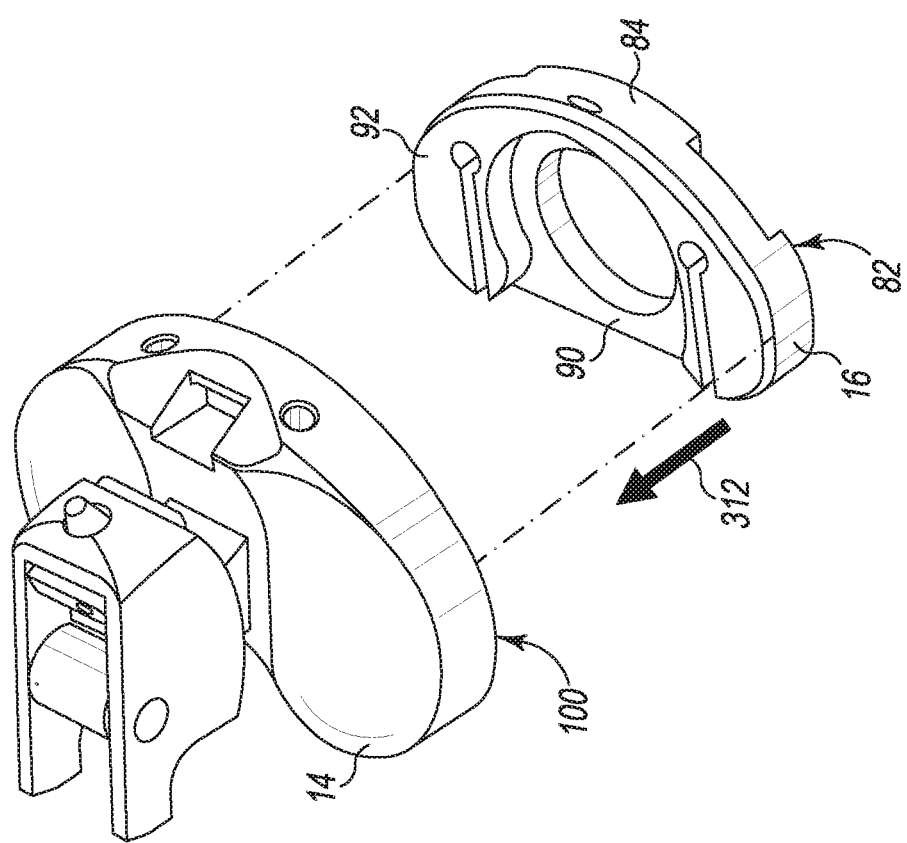
FIG. 11 is a perspective view of a trial shim being attached to a hinged tibial insert trial of FIG. 1.

As illustrated in FIG. 11, the surgeon may select a trial shim 16 for use with the hinged tibial insert trial 14. As described above, trial shims 16 may be provided in different sizes and/or configurations. The combined thickness of a particular trial shim 16 and hinged tibial insert trial 14 corresponds to the thickness of a particular tibial insert prosthetic component. The surgeon may, for example, select the trial shim 16 and/or the hinged tibial insert trial 14 to achieve a thickness determined during joint evaluation with the spacer block 306 as shown in FIG. 9. It should be understood that in some embodiments, the hinged tibial insert trial 14 may be used without a trial shim 16.

Still referring to FIG. 11, the selected trial shim 16 may be aligned with the inferior surface 100 of the hinged tibial insert trial 14. The surgeon advances the trial shim 16 in the direction indicated by arrow 312, and the superior plateau 92 of the trial shim 16 is received by the recess 126 of the hinged tibial insert trial 14. The inner walls 124 of the hinged tibial insert trial 14 engage the outer wall 84 of the trial shim 16 and thus retain the trial shim 16 against the inferior surface 100 of the hinged tibial insert trial 14. When assembled, the central passageway 94 of the trial shim 16 is aligned with the central opening 130 of the hinged tibial insert trial 14. Depending on thickness of the shim 16, the inferior surface 82 of the trial shim 16 may extend outward beyond the inferior surface 100 of the hinged tibial insert trial 14. The surgeon may remove the trial shim 16 (for example, to attach a different trial shim 16 having a different thickness) by grasping the ledge 90 on the posterior section 88 of the trial shim 16 and separating the hinged tibial insert trial 14 from the trial shim 16.

Figure 12:
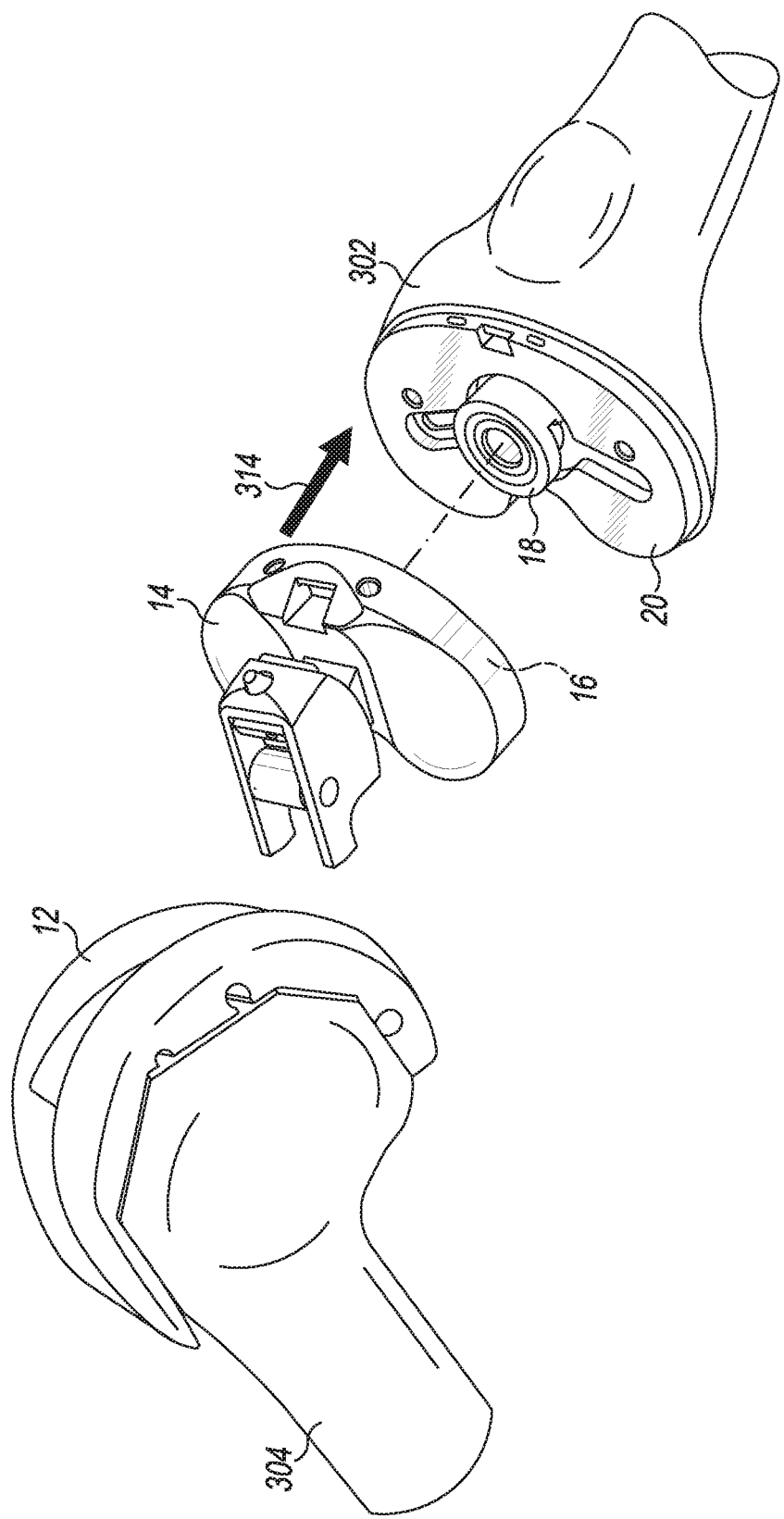
FIG. 12 is a perspective view of the hinged tibial insert trial of FIG. 1 being attached to the tibial base trial post adapter shown in FIG. 10.

As illustrated in FIG. 12, after assembly with the trial shim 16, the hinged tibial insert trial component 14 is aligned with the base post adapter 18 and the tibial base trial 20. The surgeon advances the hinged tibial insert trial component 14 in the direction indicated by arrow 314 onto the base post adapter 18. The outer surface 58 of the base post adapter 18 is received by the central opening 130 of the hinged tibial insert trial 14 and/or by the central passageway 94 of the trial shim 94. Positioning the hinged tibial insert trial component 14 on the base post adapter 18 permits the hinged tibial insert trial component 14 to rotate relative to the tibial base trial 20.

Figure 13:
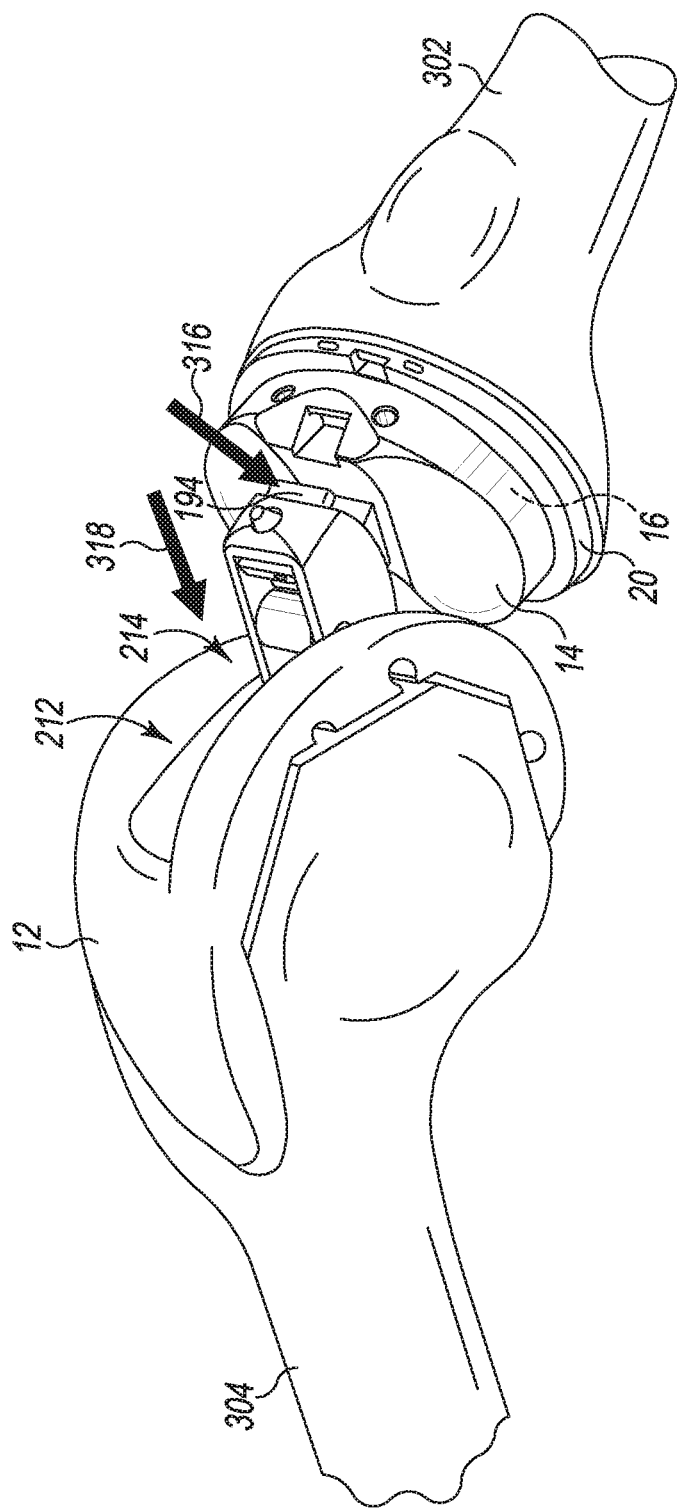
FIG. 13 is a perspective view of the hinged tibial insert trial shown in FIG. 12 being inserted into the femoral component.

After being positioned on the tibial base trial 20, the hinged tibial insert trial component 14 may be attached to the femoral trial 12. As illustrated in FIG. 13, the surgeon positions the patient's knee joint at 45 degrees of flexion or less. The surgeon depresses the button surface 194 in the direction indicated by arrow 316, causing the pointed end 186 of the plunger pin 172 to retract within the housing 136. With the button surface 194 of the push release system 170 depressed, the housing 136 is inserted into the femoral box 212 in the direction indicated by arrow 318. When the housing 136 is initially inserted, the anterior wall 156 may be tilted in an inferior direction toward the curved surfaces 104, 106. During or after insertion, the housing 136 may be rotated back such that the posterior hooks 148, 150 move in the inferior direction toward the curved surfaces 104, 106. Thus, as the housing 136 is inserted, the curved surfaces 152, 154 of the hooks 148, 150 engage the surfaces 218, 220 of the shelves 216 projecting within the femoral box 212. When fully inserted, the housing 136 engages the superior wall 208 of the femoral component. The surgeon releases the button surface 194, and the pointed end 186 is urged by the spring 174 to extend out of the housing 136 into the pocket 222 of the femoral component, thus retaining the housing 136 within the femoral component 12.

Figure 14:
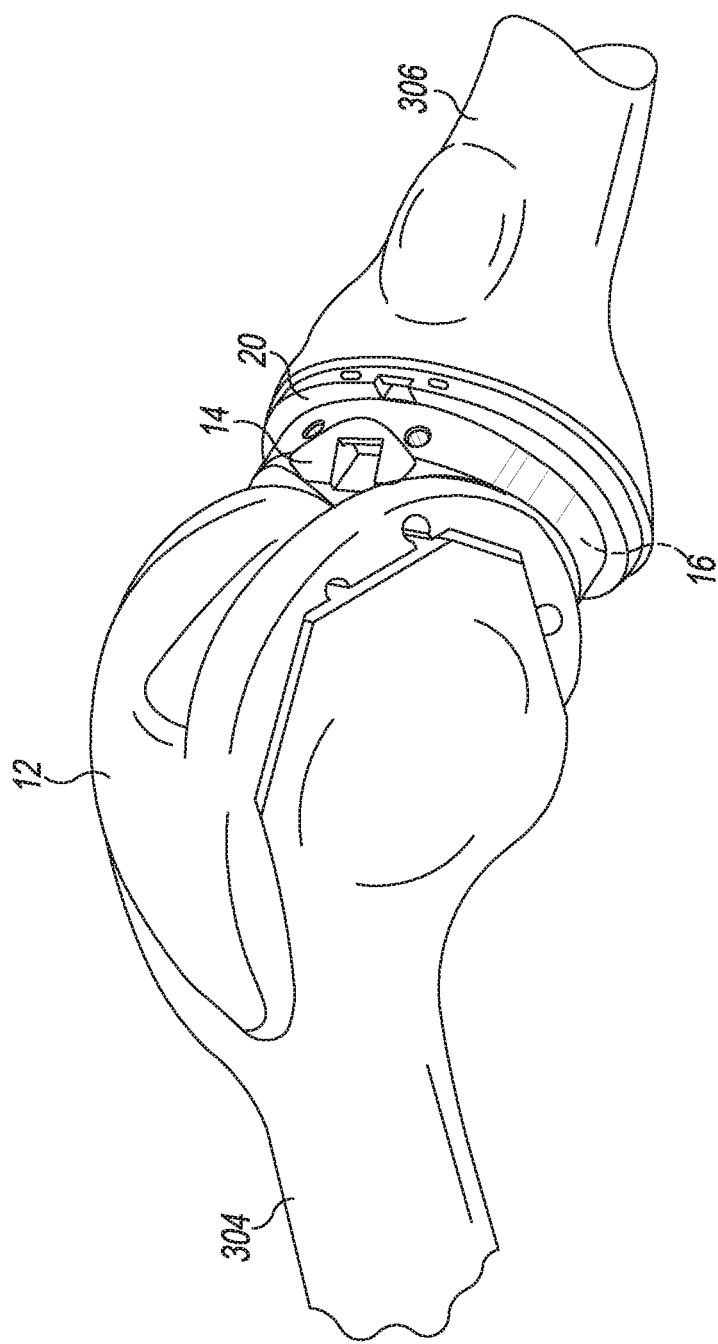
FIG. 14 is a perspective view of the assembled orthopaedic surgical instrument system of FIG. 1 positioned in the surgically prepared knee joint.

As illustrated in FIG. 14, after attaching the hinged tibial insert trial 14 to the femoral trial 12, the surgeon evaluates the knee joint. For example, the surgeon may carefully extend the knee of the patient, noting the anteroposterior stability, medial-lateral stability, and overall alignment in the anterior-posterior ("A/P") plane and medial-lateral ("M/L") plane. The hinged tibial insert trial component 14 may also be rotated about the axis 38 of the post 36 of the tibial base trial 20.

Figure 15:
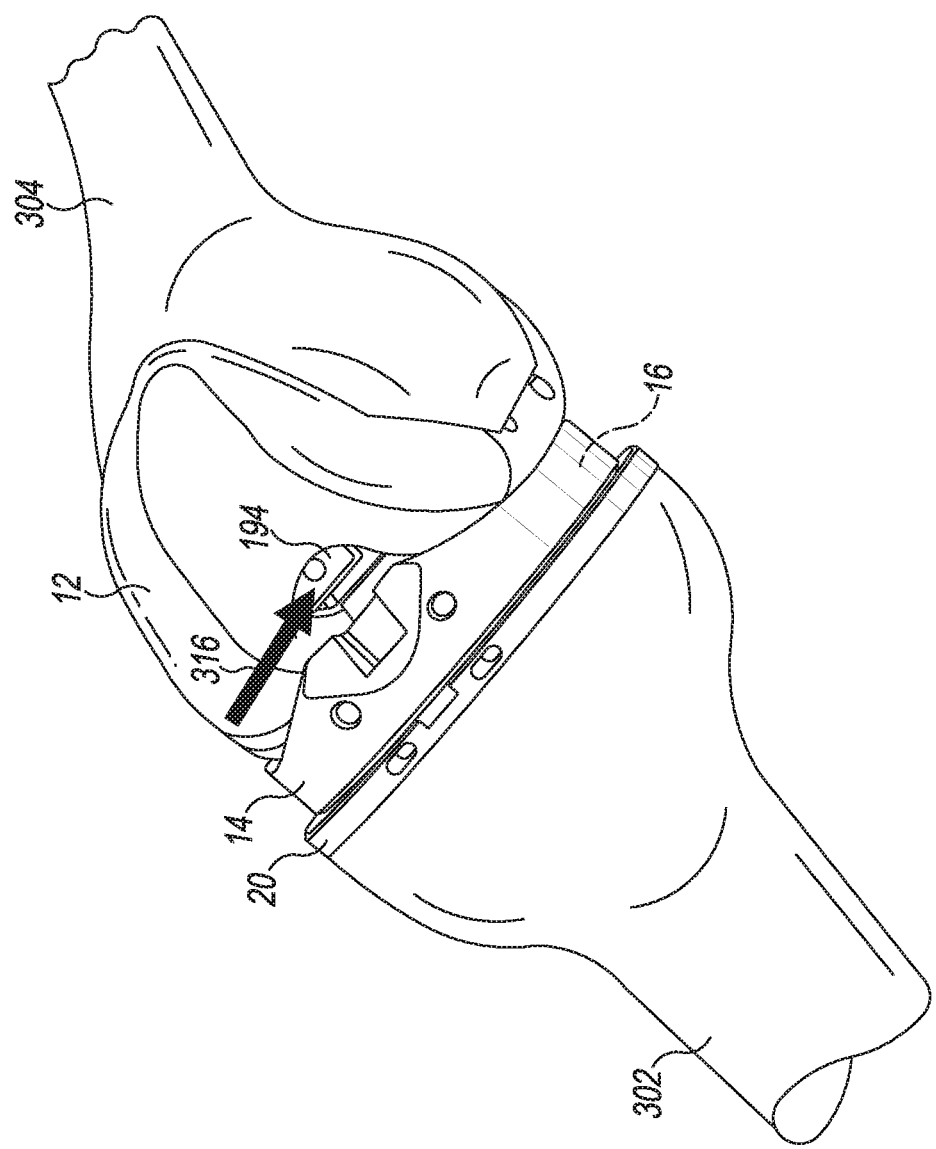
FIGS. 15-16 are perspective views of the hinged tibial insert trial shown in FIG. 14 being removed from the femoral component.
Figure 16:
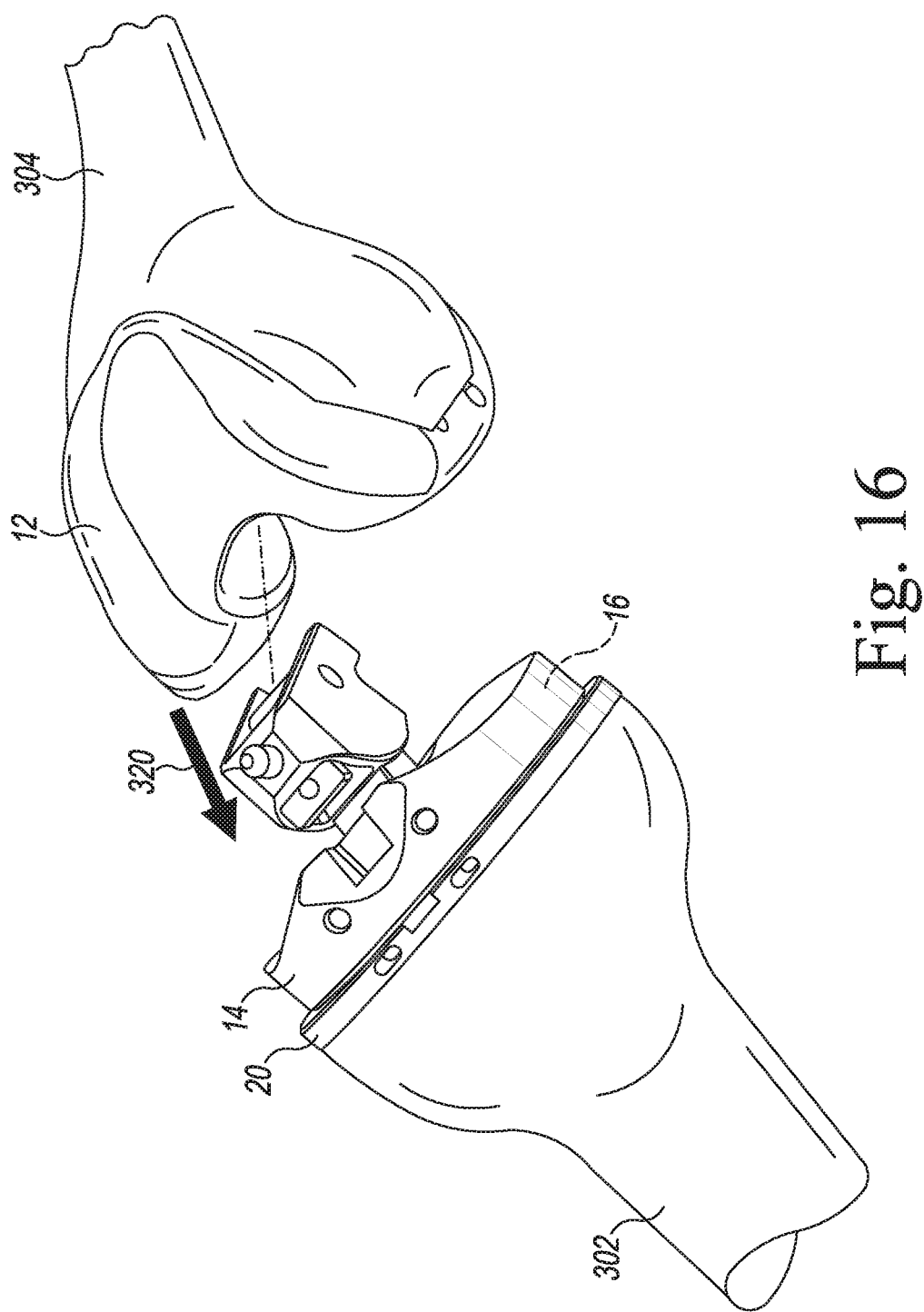

After evaluating the knee joint, the surgeon removes the hinged tibial insert trial 14, for example to exchange the hinged tibial insert trial 14 and/or the trial shim 16. As illustrated in FIG. 15, the surgeon positions the patient's knee joint at 45 degrees of flexion or less. The surgeon depresses the button surface 194 in the direction indicated by the arrow 316, causing the pointed end 186 of the plunger pin 172 to retract within the housing 136. As illustrated in FIG. 16, with the button surface 194 of the pushbutton release system 170 depressed, the surgeon removes the hinged tibial insert trial 14 from the femoral component 12 in the direction indicated by arrow 320. After being detached from the femoral component 12, the hinged tibial insert trial 14 (including any attached trial shim 16) may be removed from the base post adapter 18 by being advanced superiorly. The base post adapter 18 is left secured to the post 36 of the tibial base trial 20 such that another hinged tibial insert trial 14 and/or another trial shim 16 may be secured to the base post adapter 18 for trialing. The surgeon may then select a second hinged tibial insert trial 14 and/or a second trial shim 16 to attach to the base post adapter 18. The surgeon may then trial the second hinged tibial insert trial 14 and/or the second trial shim 16 as discussed above.

Although the retention device 15 is illustratively shown as a pushbutton release system 170, it should be appreciated that in other embodiments the retention device 15 may take other forms. For example, the tibial insert trial component 14 might include other retained fasteners such as, for example, a threaded screw, which may be received in a corresponding threaded bore in the femoral trial component 12. In other embodiments, the fastener may not be retained and/or may not be threaded. In still other embodiments, the fastener might be incorporated into the femoral trial component 12, and the tibial insert trial component 14 might include the bore configured to receive the fastener. Similarly, the plunger pin 172 and pushbutton release system 170 might be included in the femoral trial component 12, while the tibial insert trial component 14 has the pocket 222 sized to receive the plunger pin 172.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:
1. An orthopaedic surgical instrument system comprising:
a tibial base trial including a plate configured to be positioned on a proximal end of a patient's tibia and a post extending outwardly from a superior surface of the plate;
a hinged tibial insert trial including (i) an inferior surface configured to confront the superior surface of the plate, (ii) a pair of curved surfaces positioned opposite the inferior surface, (iii) a spine positioned between the pair of curved surfaces, (iv) a housing hingedly coupled to the spine and including a button mechanism having an elongated plunger pin, and (v) a central opening defined in the inferior surface;

a post adapter sized to be positioned in the central opening defined in the hinged tibial insert trial, the post adapter including an outer wall and an aperture defined in the outer wall and sized to receive the post of the tibial base trial; and a femoral component including (i) a pair of curved surfaces configured to confront the pair of curved surfaces of the hinged tibial insert trial, (ii) an anterior flange positioned between the pair of curved surfaces, (iii) a femoral box defined between the pair of curved surfaces and configured to receive the housing of the hinged tibial insert trial, and (iv) a pocket defined in an inner wall of the anterior flange and configured to receive a first end of the elongated plunger pin;

wherein the button mechanism is operable to retract the first end of the elongated plunger pin from a first position in which the first end extends outside of the housing and into the pocket defined in the inner wall of the anterior flange of the femoral component to a second position in which the first end is positioned within the housing.

2. The orthopaedic surgical instrument system of claim 1, wherein the post adapter includes a locking tab positioned in a central passageway defined in the post adapter.

3. The orthopaedic surgical instrument system of claim 2, wherein:
the post includes a stem extending outwardly from the plate to a superior flange, and
the locking tab includes a pair of arms configured to engage the stem of the post, wherein each arm of the pair of arms is a spring clip.

4. The orthopaedic surgical instrument system of claim 1, wherein:
the housing includes a medial wall having a transverse bore defined in the medial wall and extending in a medial-lateral direction and a lateral wall having a transverse bore defined in the lateral wall and extending in the medial-lateral direction;
the spine includes a transverse bore extending in the medial-lateral direction; and
the hinged tibial insert trial includes an elongated pin positioned in the transverse bores of the housing and the spine to couple the housing to the spine.

5. The orthopaedic surgical instrument system of claim 4, wherein the housing of the hinged tibial insert trial is configured to rotate about an axis extending through the elongated pin.

6. The orthopaedic surgical instrument system of claim 1, further comprising a trial shim including (i) an inferior surface configured to confront the superior surface of the plate, (ii) a superior surface including a superior plateau sized to be received by a recess defined in the inferior surface of the hinged tibial insert trial, and (iii) a central passageway defined in the trial shim and sized to receive the post adapter.

7. The orthopaedic surgical instrument system of claim 1, wherein:
the housing comprises a hook extending posteriorly and including a curved inferior surface; and
the femoral component comprises a shelf extending into the femoral box and including a curved superior surface configured to confront the curved inferior surface of the housing.

8. The orthopaedic surgical instrument system of claim 1, wherein the femoral component comprises a prosthetic implant.

9. The orthopaedic surgical instrument system of claim 1, wherein:
the housing comprises an anterior wall having a bore defined in the anterior wall;
the first end of the elongated plunger pin selectively extends through the bore in the anterior wall; and
the button mechanism comprises a spring configured to bias the first end of the elongated plunger pin to extend through the bore.

10. The orthopaedic surgical instrument system of claim 9, wherein:
the housing comprises a medial wall and a lateral wall, wherein the medial wall, the lateral wall, and the anterior wall cooperate to define a button chamber accessible through the bore in the anterior wall, and wherein the button mechanism is positioned within the button chamber; and
the button mechanism comprises a button plate coupled to the elongated plunger pin and extending through an inferior opening in the button chamber.

* * * * *